United States Patent [19]
Marks et al.

[11] Patent Number: 5,080,104
[45] Date of Patent: Jan. 14, 1992

[54] PROXIMITY DETECTOR WITH A MEDICAL INSTRUMENT

[75] Inventors: Ronald Marks; Christopher Edwards, both of Cardiff, Great Britain

[73] Assignee: University of Wales College of Medicine, Cardiff, United Kingdom

[21] Appl. No.: 312,704

[22] PCT Filed: Aug. 3, 1987

[86] PCT No.: PCT/GB87/00551
§ 371 Date: Jan. 30, 1989
§ 102(e) Date: Jan. 30, 1989

[87] PCT Pub. No.: WO88/00811
PCT Pub. Date: Feb. 11, 1988

[30] Foreign Application Priority Data
Aug. 5, 1986 [GB] United Kingdom ............... 8619107
Apr. 16, 1987 [GB] United Kingdom ............... 8709279

[51] Int. Cl.⁵ ............................................. A61B 8/14
[52] U.S. Cl. ............................... 128/662.05; 604/116
[58] Field of Search ............. 128/303 R, 630, 668, 128/662.05, 897, 903, 773, 715, 662.06, 24 A; 604/116-117

[56] References Cited

U.S. PATENT DOCUMENTS

| | | | |
|---|---|---|---|
| 3,745,989 | 7/1973 | Pinna | 128/668 |
| 4,175,567 | 11/1979 | Patel | 128/748 |
| 4,248,241 | 2/1981 | Tacchi | 128/903 X |
| 4,344,436 | 8/1982 | Kubota | 128/773 X |
| 4,527,569 | 7/1985 | Kolb | 604/116 X |
| 4,535,773 | 8/1985 | Yoon | 128/630 X |
| 4,667,679 | 5/1987 | Sahota | 604/116 X |
| 4,804,054 | 2/1989 | Howson et al. | 128/897 X |

FOREIGN PATENT DOCUMENTS
0190719 8/1986 European Pat. Off. .
2142163 1/1985 United Kingdom .

Primary Examiner—Max Hindenburg
Attorney, Agent, or Firm—Young & Thompson

[57] ABSTRACT

A surgical or medical implement including a proximity detector to indicate the distance from an internal organ or member such as an artery. In one form the invention is applied to a surgical scalpel (12) with an audio transducer in contact with the blade (11) and connected to an electrical circuit (18) for providing a warning signal. In another form the invention is applied to a hypodermic syringe (50) with a transducer (60) in contact with the needle (56) and connected through circuitry (62) with a warning lamp or buzzer (63,64).

13 Claims, 3 Drawing Sheets

PROXIMITY DETECTOR WITH A MEDICAL INSTRUMENT

BACKGROUND OF THE INVENTION

This invention relates to a proximity detector which is primarily, though not exclusively, applicable to surgical or medical implements.

In surgical operations there is a risk, however careful the surgeon may be, of accidentally incising or damaging parts of the body such as arteries, viscera or nerves. Likewise when giving an injection by means of a hypodermic needle or the like, there may be a similar risk of causing such damage, but more importantly the invention can be applied in a contrary sense to assist in penetrating the artery.

SUMMARY OF THE INVENTION

Accordingly, it is one object of the invention to provide an instrument with means for producing a warning or control signal which will assist the surgeon or medical personnel in avoiding such damage, and/or in locating an internal target such as an artery.

From one aspect the invention consists in a proximity detector in conjunction with a surgical or medical instrument or the like, comprising an audio transducer positioned on or adjacent to the implement or a part thereof for detecting sounds or changes in pressure levels in the surrounding zone, and a response or actuatory system coupled to the transducer to provide an output related to the position of the implement relative to another object or body of interest, such as an artery.

In one preferred form of the invention the detector is designed to sense pulses created or existing within the body being operated upon, and by appropriate electronic circuitry to sense or measure the proximity of the body from the source of the pulsing input to the transducer.

For example, in the case of a blood artery, the arterial pulses produce cyclic sound signals which can be detected by an audio-electronic transducer. In some preferred systems according to the invention the detector is arranged in conjunction with a surgical implement, the audio transducer being mounted on or in contact with the cutting blade or other tool. Alternatively, in the case of a hypodermic needle or syringe the transducer may be positioned in good acoustic contact with the needle.

To reduce or eliminate extraneous "noise" or other pressure variations, the transducer is preferably coupled or connected to a comparator circuit having a second input derived from a different point on the body of the patient or other zone, such that the comparator output is representative of the local sound signals only.

In any case, the apparatus preferably includes an amplifier coupled to the transducer and means responsive to the output of the amplifier to determine the distance between the implement and a pre-selected object.

In some forms of the invention the apparatus includes an audible, visual or tactile warning device to indicate proximity of the instrument to an artery or viscera. Alternatively, there may be an automatic control system or actuator for positively preventing further incision or penetration by the implement.

According to another preferred feature of the invention, the apparatus includes a radio transmission link between the audio transducer and a remote comparator, or warning, indicating or control device.

As previously mentioned the invention may be applied to a hypodermic syringe and needle, in which case the detector is used to assist the user in finding and penetrating an artery rather than avoiding it.

Broadly stated from this aspect the invention consists in a hypodermic syringe and needle including an audio transducer acoustically coupled with the needle to sense pressure changes or vibrations in tissue adjacent to the needle.

As applied to a hypodermic syringe and needle it is often useful or important for the user to know that the tip of the needle is in the proper position for making an injection, often into an artery. Thus the transducer is preferably arranged to detect and indicate proximity of the needle to an artery, and it may be arranged to detect when the needle has actually penetrated an artery.

In a particular preferred construction the transducer is located in close contact with the base of the needle so that vibrations experienced at the tip of the needle are conveyed along the length of the needle and by direct or indirect contact to the transducer.

It is of advantage that the invention can be applied to existing standard syringes and needles and in a particular preferred arrangement the syringe is located at least partly within a holder which has an aperture through which the needle projects and the holder also incorporates an amplifier, a visible or audible warning indicator and a battery or other power source.

DESCRIPTION OF THE DRAWINGS

The invention may be performed in various ways and three specific embodiments, with a number of possible modifications, will now be described by way of example with reference to the accompanying drawings, in which.

DESCRIPTION OF THE PREFERRED EMBODIMENTS

In the first example the invention is applied to a surgeon's scalpel as illustrated at 10, having a knife or blade 11, usually formed of stainless steel. In this example the handle of the scalpel is positioned in a holder 12 which is provided with a closure or lid 9 and an audio transducer 13 pressed into close contact with the handle of the scalpel so as to detect any sound or other vibrations. This transducer is conveniently a piezo-electric crystal or ceramic such as a p.z.t (lead zirconate titanate) ceramic transducer.

Figure 1:
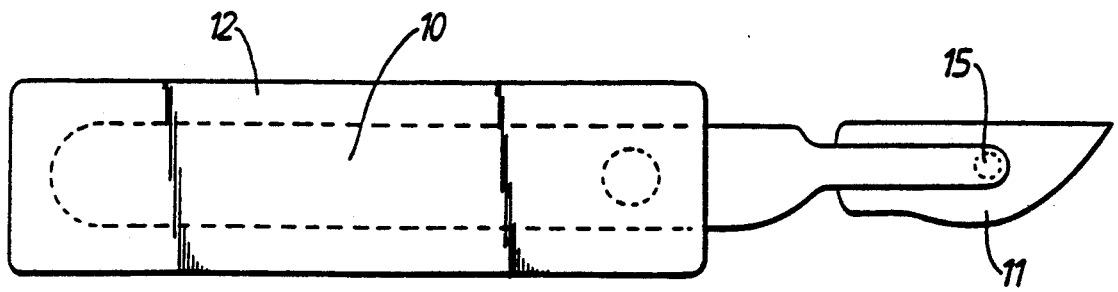
FIG. 1 is a diagrammatic illustration of a surgeon's scalpel in a handle or holder, and provided with a miniature acoustic transducer according to the invention.
Figure 2:
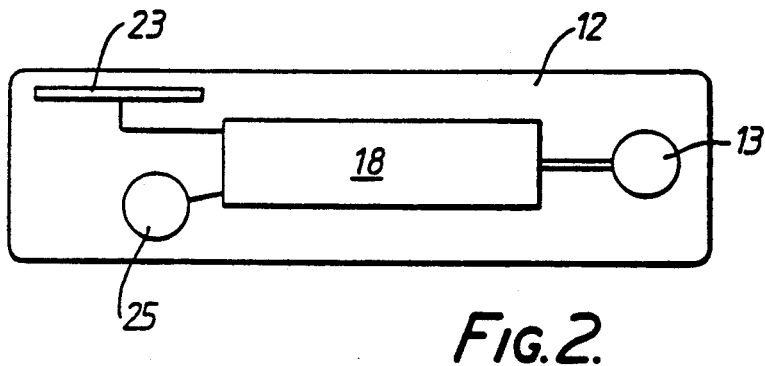
FIG. 2 is a very diagrammatic illustration of the essential components of the transducer system.
Figure 3:
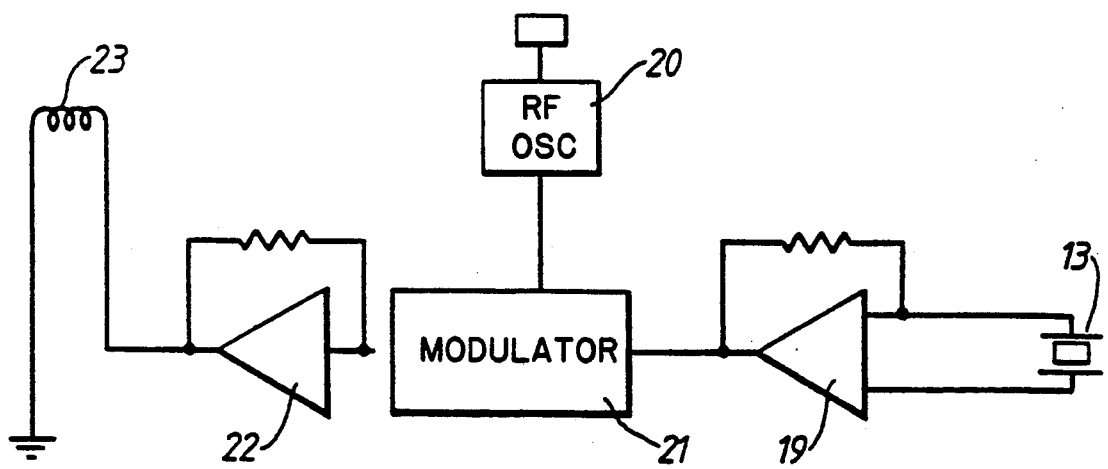
FIG. 3 is a diagram illustrating the essentials of the electronic circuit.

Alternatively, the transducer may be positioned as shown at 15 directly on the blade or other part of the scalpel. The transducer is electrically coupled to circuitry illustrated at 18 and in more detail in FIG. 3, which includes a preamplifier 19, an R.F. oscillator 20, a modulator 21, R.F. amplifier 22 and a small ferrite transmitting aerial 23. The handle 12 also includes a small battery 25 for the electronic circuit.

Figure 4:
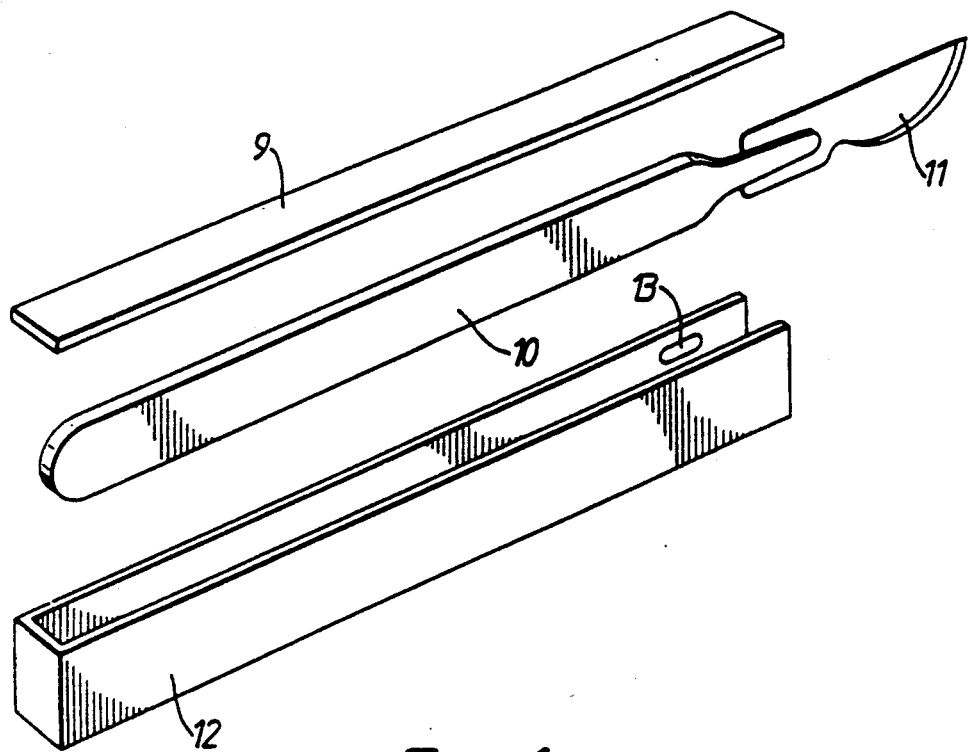
FIG. 4 is an exploded view illustrating the same constructional elements in a typical example.

In the diagrammatic illustration of FIG. 4 the scalpel handle 10 is mounted in a holder 12 of box or trough shape and is clamped in position in contact with the audio transducer 13, which is spring-urged into contact with the handle. The scalpel itself with its blade 11 can be removed to be sterilized and replaced, or it may be disposable, and the holder 12 with the transducer and other elements of the circuit of 18 is preferably separate from the instrument and need not therefore be treated as disposable.

The information transmitted by the antenna 23 will include all vibrations or sounds picked up by the transducer and this will include, for example, noise created by the actual cutting action of the scalpel through tissue. In some cases that sound itself may be sufficient to trigger a warning signal, in which case the warning circuit merely includes a level detector sensitive to the volume of sound received.

Figure 5:
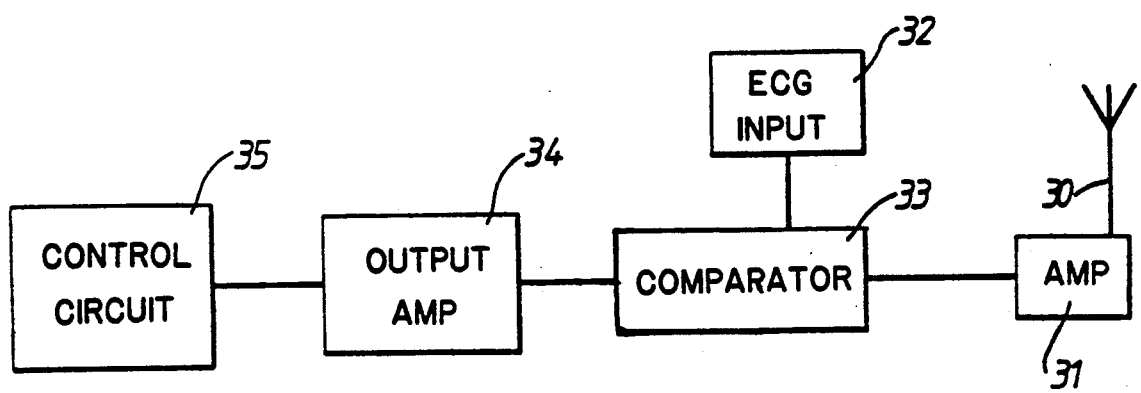
FIG. 5 is a further diagram illustrating the associated electronic comparator warning circuit coupled to an E.C.G. (electro-cardiograph) instrument.

In a preferred construction, however, the detector relies on the sounds and vibrations created by the pulsing flow of blood in the artery or viscera and the apparatus includes the further equipment illustrated in FIG. 5. This is positioned adjacent to but not physically connected to the surgeon's scalpel and includes a receiving antenna 30, an amplifier 31, E.C.G. (Electro-Cardiograph) input 32, a comparator or lock-in amplifier 33, output amplifier 34 and warning or control circuit 35. The lock-in amplifier 33 compares the signal received from the E.C.G. with the signal transmitted between the radio link 23,30, eliminates extraneous "noise" and thus detects only the vibrations of interest, in this case the artery pulse, and then responds to a pre-selected level which is related to the distance between the scalpel blade and the actual artery. At the required level of proximity the alarm is activated.

Figure 6:
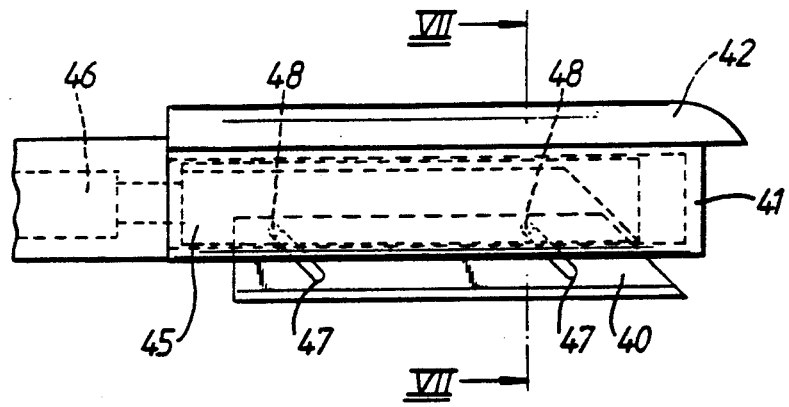
FIG. 6 is a further diagram illustrating a possible modification with the sensor separate from the blade of the instrument.
Figure 7:
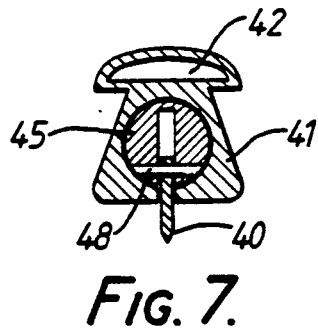
FIG. 7 is a diagrammatic cross-section through the implement on the lines VII—VII in FIG. 6.

In the alternative illustrated in FIGS. 6 and 7 the instrument comprises a detachable blade 40, mounted in a blade carrier 41 with the proximity sensor or probe 42 positioned above the carrier and close to the blade but not in direct contact. In this case the instrument includes an automatic withdrawal mechanism comprising a plunger 45 movable lengthwise by a hydraulic, mechanical or electrical actuator 46, preferably with a return spring. The plunger has a pair of inclined cam slots 47 engaged by pins 48 attached to the blade, and on receipt of the warning signal from the output element of the comparator circuit, the plunger is triggered to cause the blade 40 to withdraw into the holder 41.

Figure 8:
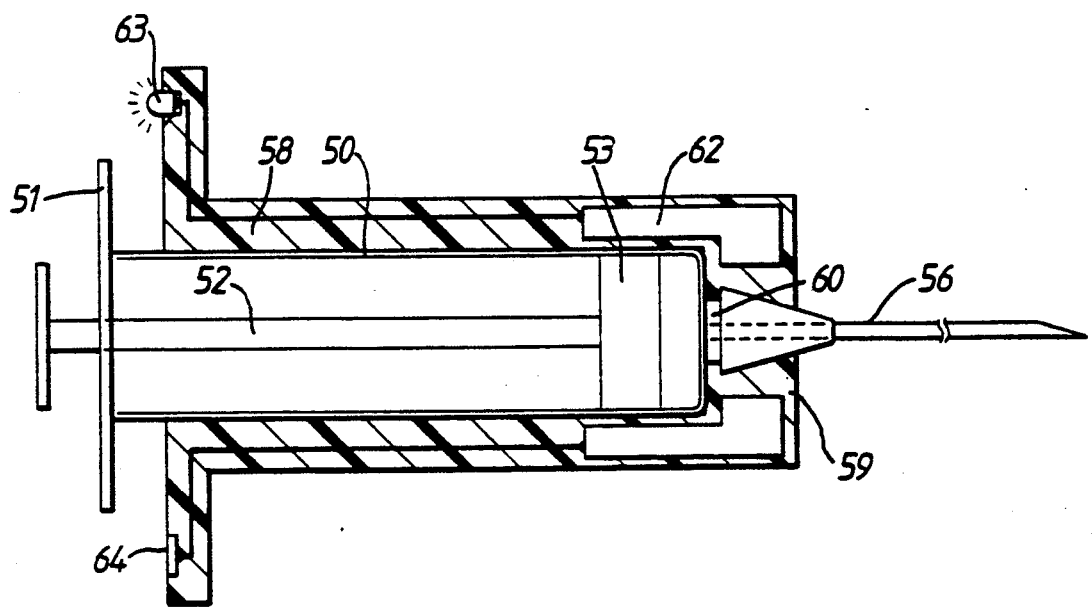
FIG. 8 is a diagrammatic sectional elevation through a modified hypodermic syringe and needle according to the invention.

In the example of FIG. 8 the invention is applied to a standard hypodermic syringe assembly comprising a cylinder 50 having a cover or closure 51 at its rear end with an aperture to receive the rod 52 of the piston 53. At the other end of the cylinder a further opening is provided to receive and locate the base of the hypodermic needle 56. The needle is normally secured permanently to the cylinder and is disposable as one unit or it may be removable.

In accordance with the invention the cylinder 50 is located within a holder 58 which is also generally cylindrical and has an end wall 59 formed with an aperture through which the needle projects. This end wall also supports an acoustic transducer 60 which in this example is a generally flat annular disc designed to make intimate contact with the base of the needle when in position thus allowing good acoustic transmission from the needle to the transducer. The holder also includes an electronic compartment 62 which may comprise a miniaturized amplifier coupled with a volume or amplitude threshold detector arranged to provide an output signal when the volume of sound or vibration reaching the transducer reaches a predetermined value. The output of this signalling circuit is connected to a warning or indicator device such as a small L.E.D. light 63 and/or an audible warning buzzer 64. These are preferably positioned on lateral projections from the holder so as to give a clear warning to the person using the syringe and the threshold level is preferably set or adjusted to a value which corresponds to the tip of the needle penetrating the wall of an artery. This then indicates that the needle is in proper position for the injection. Alternatively the circuit may be set or adjusted to give warning that the tip of the needle is in close proximity with an artery.

It will be appreciated that the holder and related components may be manufactured separately from a standard syringe and designed to be readily coupled thereto, for example by simply inserting the syringe and needle into the holder.

It will be understood that the invention can thus be applied to detect the proximity of vascular orvvisceral structures in general or blood vessels or nerves, or other sensitive parts of the body and the associated sensing circuitry may be designed and adjusted to operate at any required distance or indeed to detect or prevent incision or cutting into a body up to or beyond any pre-set depth.

What is claimed is:

1. A hypodermic syringe and needle assembly, characterized by an audio transducer acoustically coupled with a needle of said hypodermic syringe and needle assembly to sense audio frequency pressure changes or vibrations in tissue adjacent to the needle, at least part of the needle acting to transmit said pressure changes or vibrations to said transducer, and means sensitive to the amplitude of an output of said transducer to indicate the proximity of the needle to an object of interest.

2. A syringe and needle assembly according to claim 1, characterized in that the transducer is connected to a signalling device to indicate the proximity of the needle to an object creating pressure changes or vibrations.

3. A syringe and needle assembly according to claim 2, characterized in that the transducer is coupled through an amplifier to an audible or visible signalling device positioned on or attached to the syringe.

4. A syringe and needle assembly according to claim 1, characterized in that the transducer is arranged to detect and indicate proximity of the needle to an artery, or that the needle has penetrated an artery.

5. A syringe and needle assembly according to claim 1, characterized in that the transducer is located in close contact with the base of the needle so that vibrations experienced at the tip of the needle are conveyed along the length o the needle and by direct or indirect contact to the transducer.

6. A syringe and needle assembly according to claim 1, characterized in that said hypodermic syringe is located at least partly within a holder which has an aperture through which the needle projects and the holder also incorporates an amplifier, a visible or audible warning indicator and a battery or other power source.

7. A hypodermic syringe and needle assembly according to claim 1, further comprising a holder or support attached thereto for said audio transducer.

8. The combination of a proximity detector and a surgical or medical implement designed to penetrate a living body, the proximity detector comprising an audio transducer carried by the implement for detecting sounds or audio frequency changes in pressure levels in a surrounding zone of said living body, and a response or actuator system coupled to the transducer to provide an output related to the amplitude of the transducer output and hence to the position of the implement relative to another object of interest within said body.

9. The combination claimed in claim 8, wherein said implement has a cutting blade or penetrating point and said audio transducer is mounted on or in contact with said blade or point.

10. The combination claimed in claim 8, wherein said audio transducer is coupled or connected to a comparator circuit having an input derived from a different point in said body.

11. The combination claimed in claim 8, further comprising an amplifier coupled to the audio transducer and means responsive to the amplitude at the output of the amplifier to determine the distance between the implement and said object of interest.

12. The combination claimed in claim 8, further comprising an audible, visual or tactile warning device to indicate proximity of the implement to an artery or viscera.

13. The combination claimed in claim 8, further comprising a radio transmission link between the audio transducer and a remote comparator or warning or indicating or control device.

* * * * *